United States Patent [19]

Asato et al.

[11] Patent Number: 5,019,589

[45] Date of Patent: * May 28, 1991

[54] $\Delta^{23}$-LL-F28249 COMPOUNDS

[75] Inventors: Goro Asato, Titusville; Zareen Ahmed, Princeton Junction, both of N.J.

[73] Assignee: American Cyanamid Company, Stamford, Conn.

[ * ] Notice: The portion of the term of this patent subsequent to Aug. 21, 2007 has been disclaimed.

[21] Appl. No.: 907,187

[22] Filed: Sep. 12, 1986

[51] Int. Cl.$^5$ .................. A61K 31/365; C07D 313/00
[52] U.S. Cl. ...................................... 514/450; 549/264
[58] Field of Search .......................... 549/264; 514/450

[56] References Cited

U.S. PATENT DOCUMENTS

| | | | |
|---|---|---|---|
| 4,172,075 | 10/1979 | Biolaz et al. | 540/69 |
| 4,328,335 | 5/1982 | Mrozik | 536/7.1 |
| 4,587,247 | 5/1986 | Linn et al. | 549/264 |

FOREIGN PATENT DOCUMENTS

| | | |
|---|---|---|
| 170006 | 2/1986 | European Pat. Off. . |
| 2166436 | 5/1986 | United Kingdom . |

OTHER PUBLICATIONS

Burgess et al., J. Org. Chem., vol. 38(1), pp. 26–31, 1973.
Michael J. Green et al., Jour. Chem. Soc., Chem. Comm. (1977), pp. 611–612.
Lila Somekh et al., J. Org. Chem., vol. 48 (6), (1983), pp. 907–908.

*Primary Examiner*—C. Warren Ivy
*Assistant Examiner*—Ba K. Trinh
*Attorney, Agent, or Firm*—Estelle J. Tsevdos

[57] ABSTRACT

The present invention relates to novel derivatives of LL-F28249 compounds wherein the 23-hydroxy group is eliminated to introduce a double bond at the 23,24 position. These resulting derivatives are $\Delta^{23}$-LL-F28249 compounds. These LL-F28249 precursor compounds preferably are derived via a controlled microbiological fermentation of *Streptomyces cyaneogriseus* subsp. *noncyanogenus* having deposit accession number NRRL 15773. The novel derivatives of the present invention possess activity as anthelmintic, ectoparasitic, insecticidal, acaricidal and nematicidal agents. They also are useful in areas of human and animal health and in agricultural crops.

14 Claims, No Drawings

$\Delta^{23}$-LL-F28249 COMPOUNDS

BACKGROUND OF THE INVENTION

The present invention relates to new derivatives of the antibiotics collectively defined as LL-F28249. These antibiotics preferably are produced by the fermentation of the microorganism *Streptomyces cyaneogriseus* subsp. *noncyaneogenus*, deposited in NRRL under deposit accession no. 15773. The LL-F28249 compounds and the method for their production are disclosed in European Patent Application Publication No. 170,006, incorporated herein by reference.

The present invention further relates to methods and compositions for preventing, treating or controlling helmintic, ectoparasitic, insect, acarid, and nematode infections and infestations in warm-blooded animals and agricultural crops by administering thereto prophylactically, therapeutically or pharmaceutically effective amount of the present $\Delta^{23}$-LL-F28249 agents (compounds), mixtures thereof or the pharmaceutically and pharmacologically-acceptable salts thereof.

These infections not only cause devastating effects to animals but also seriously effect the economics of farmers in raising meat-producing animals such as swine, sheep, cattle, goats, rabbits and poultry. Further, such infections are a source of great concern for companion animals such as horses, dogs and cats. Therefore, effective methods for the treatment and prevention of these diseases constantly are being sought.

SUMMARY OF THE INVENTION

The present invention provides novel derivatives of the compounds designated LL-F28249 and represented by the following structural formula,

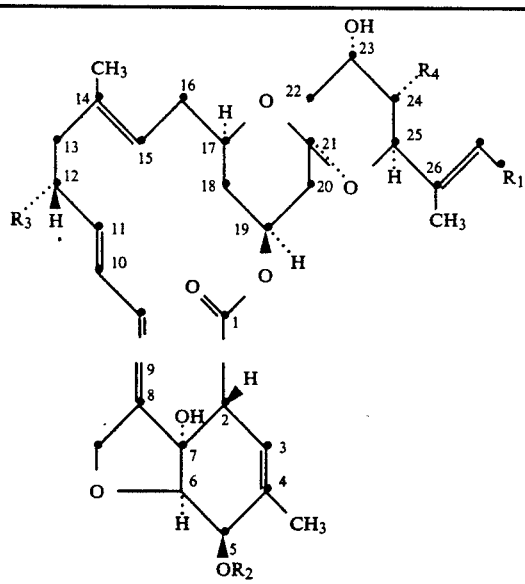

| Component | $R_1$ | $R_2$ | $R_3$ | $R_4$ |
| --- | --- | --- | --- | --- |
| LL-F28249α | CH(CH$_3$)$_2$ | H | CH$_3$ | CH$_3$ |
| LL-F28249β | CH$_3$ | H | CH$_3$ | CH$_3$ |
| LL-F28249γ | CH$_3$ | CH$_3$ | CH$_3$ | CH$_3$ |
| LL-F28249ε | CH(CH$_3$)$_2$ | H | H | CH$_3$ |
| LL-F28249δ | CH$_2$CH$_3$ | H | CH$_3$ | CH$_3$ |
| LL-F28249θ | CH(CH$_3$)$_2$ | H | CH$_3$ | CH$_2$CH$_3$ |
| LL-F28249 | CH(CH$_3$)$_2$ | H | CH$_2$CH$_3$ | CH$_3$ |
| LL-F28249λ | CH(CH$_3$)$_2$ | CH$_3$ | CH$_3$ | CH$_3$ |

The compounds of the present invention are represented by structural formula (I),

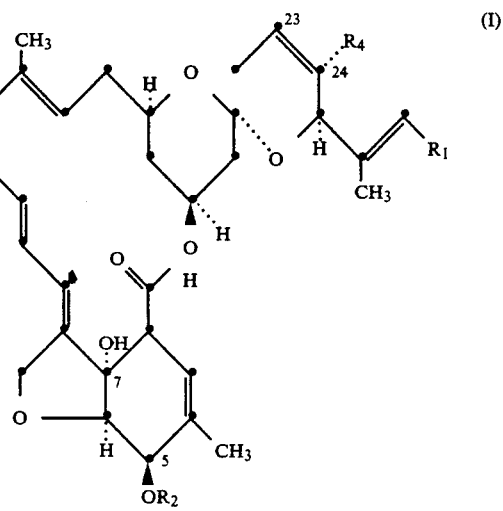

wherein $R_1$ is methyl, ethyl or isopropyl; $R_2$ is hydrogen or methyl; $R_3$ is hydrogen, methyl or ethyl; $R_4$ is methyl or ethyl; and the pharmaceutically and pharmacologically acceptable salts thereof.

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings, and agricultural crops.

Although these diseases have been recognized for years and therapies exist for the treatment and prevention of the diseases, the present invention provides novel compounds in the search for effective such therapy. For instance, U.S. Application for Letter patent Ser. Nos. 907,186; 907,187; 907,188; 907,259; 907,281 and 907,284 of Asato and Asato et al, filed concurrently herewith and incorporated herein by reference thereof, provide novel compounds for such uses.

U.S. Pat. No. 3,950,360, Aoki et al, Apr. 13, 1976, discloses certain antibiotic substances obtained by culturing a *Streptomyces* microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, June 3, 1980; U.S. Pat. No. 4,310,519, Albers-Schonberg, Jan. 12, 1982; U.S. Pat. No. 4,333,925, Buhs et al, June 8, 1982). U.S. Pat. No. 4,423,209, Mrozik, Dec. 27, 1983 relates to the process of converting some of these less desirable components to more preferred ones. British Patent Application 2166436A of Ward et al relates to antibiotics also.

The present compounds or the pharmaceutically and pharmacologically-acceptable salts thereof exhibit excellent and effective treatment and/or prevention of these serious diseases of warm-blooded animals.

It is an object of the present invention, therefore, to provide novel $\Delta^{23}$-compounds of the LL-F28249 series of compounds.

It is a further object of the present invention to provide novel methods for the treatment, prevention or control of helmintic ectoparasitic, insect, acarid and nematode infections and infestations in warm-blooded animals and agricultural crops.

It also is an object of the present invention to provide novel compositions to effectively control, prevent or treat said diseases in warm-blooded animals.

These and further objects will become apparent by the below-provided detailed description of the invention.

DETAILED DESCRIPTION OF THE INVENTION

The compounds of the invention are represented by structural formula (I),

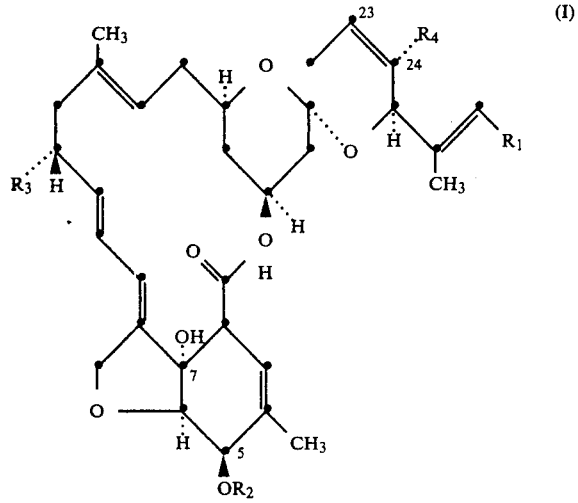

wherein $R_1$ is methyl, ethyl or isopropyl; $R_2$ is hydrogen or methyl; $R_3$ is hydrogen, methyl or ethyl; $R_4$ is methyl or ethyl; and the pharmaceutically and pharmacologically acceptable salts thereof.

Preferably, $R_1$ is isopropyl; $R_2$ is hydrogen or methyl; $R_3$ is methyl; and $R_4$ is methyl. Most preferred compound includes RI as isopropyl, $R_2$ as hydrogen, $R_3$ as methyl and $R_4$ as methyl.

The $\Delta^{23}$-LL-F28249 derivatives of the present invention are prepared by eliminating the 23-hydroxyl group and introducing a double bond at the 23-24 position.

The process involves oxidation of the 5-hydroxyl group of the appropriate LL-F28249 compound with activated $MnO_2$ in ether at room temperature (about 25° C.) to afford the 5-oxo-LL-F28249 compound. This is followed by reacting the 5-oxo-LL-F28249 compound with dialkylaminosulfur trifluoride in an inert solvent, such as dimethoxyethane, at a temperature of about $-50°$ C. to $-5°$ C. and then reducing the 5-oxo group with $NaBH_4$ in methanol or ethanol at room temperature (25° C.) to yield the 5-hydroxy-LL-F28249 components containing a double bond at the thermodynamically more stable 23-24 position ($\Delta^{23}$).

The LL-F28249 compounds with a 5-methoxy group (LL-F28249$\gamma$ and $\lambda$) are directly reacted with dialkylaminosulfur trifluoride to yield $\Delta^{23}$-LL-F28249$\gamma$ and $\lambda$, respectively.

The compounds of the present invention are useful as anthelmintics, ectoparasiticides, insecticides, acaricides and nematicides.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum primarily attack the intestinal tract, while others, such as Haemonchus and Ostertagia, are most prevalent in the stomach. Still others, such as Dictyocaulus, are found in the lungs. However, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and, if left untreated, may result in death of the infected host. The $\Delta^{23}$-LL-F28249 compound derivatives of the present invention unexpectedly have high activity against these parasites. Additionally, the compounds of this invention also are active against Dirofilaria in dogs, Nematospiroides, Syphacia, Aspiculuris in rodents, arthropod ectoparasites such as ticks, mites, lice, fleas, blowfly, of animals and birds, the ectoparasite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites (collectively includes ecto and/or endoparasites) which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle Attagenus sp. and the housefly Musca domestica.

Insect pests of stored grains such as Tribolium sp., Tenebrio sp., and of agricultural plants such as spider mites (Tetranychus sp.), aphids (Acyrthiosiphon sp.), southern army worms, tobacco budworms, boll weevils migratory orthopterans, such as locusts and immature stages of insects living on plant tissue are controlled by the present compounds, as well as the control of soil nematodes and plant parasites such as Meloidogyne sp.

The compounds of the present invention may be administered orally or parenterally for animal and human usage, while they may be formulated in liquid or solid form for agricultural use. Oral administrations may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer the $\Delta^{23}$-LL-F28249 derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the invention may be administered to animals parenterally such as by intraruminal, intramuscular, intratracheal or subcutaneous injection. In such an event, the active compound is dissolved or dispersed in a liquid carrier vehicle.

For parenteral administration, the active compound is suitably admixed with an acceptable vehicle, preferably a vegetable oil such as peanut oil, cotton seed oil or the like. Other parenteral vehicles such as organic preparations using solketal, glycerol formal and aqueous parenteral formulation also are used. The active LL-F28249 compound derivative or derivatives are dissolved or suspended in the parenteral formulation for administration. Such formulations generally contain about 0.005% to 5%, by weight, of the active compound.

Although the compounds of the present invention are primarily used in the treatment, prevention or control of helminthiasis, they also are useful in the prevention, treatment or control of diseases caused by other parasites (collectively both ecto and/or endoparasites). For example, arthropod parasites such as ticks, lice, fleas, mites and other biting insects in domesticated animals and poultry are controlled by the present compounds. These compounds also are effective in treatment of parasitic diseases which occur in other animals including human beings. The optimum amount to be employed will, of course, depend upon the particular compound employed, the species of animal to be treated and the type and severity of parasitic infection or infestation. Generally, the amount useful in oral administration of these novel compounds is about 0.001 mg to 10 mg per kg of animal body weight, such total dose being given at one time or in divided doses over a relatively short period of time (1-5 days). The preferred compounds of the invention give excellent control of such parasites in animals by administering about 0.025 mg to 3 mg per kg of animal body weight in a single dose. Repeat treatments are given as required to combat reinfections and are dependent upon the species of parasite and the husbandry techniques being employed. The techniques for administering these materials to animals are known to those skilled in the veterinary field.

When the compounds described herein are administered as a component of animals' feed or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment and control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds of this invention also are useful in combating agricultural pests that inflict damage upon growing or stored crops. The present compounds are applied, using known techniques such as sprays, dusts, emulsions and the like, to the growing or stored crops to effect protection from agricultural pests.

The present invention is illustrated by the following examples which are illustrative of said invention and not limitative thereof.

EXAMPLE I $\Delta^{23}$-5-oxo-LL-F28249α

In 1.5 mL of dry dimethoxyethane, 0.2168 g of 5-oxo-LL-F28249 is dissolved. Under $N_2$ atmosphere and at $-6°$ C., 0.1148 g of diethylaminosulfur trifluoride is added dropwise. After stirring for 15 minutes, the mixture is poured into an ice-$H_2O$ mixture and stirred for 0.5 hours. The aqueous mixture is extracted with $CH_2Cl_2$ several times, and the combined extracts are dried ($MgSO_4$) and evaporated to dryness. The residual gum is purified by chromatography on silica gel using 20:1 CH$_2$Cl$_2$/EtOAc on preparative plates to afford $\Delta^{23}$-5-oxo-LL-F28249$\alpha$ that is characterized by mass spectrometry and NMR spectroscopy.

EXAMPLE 2 $\Delta^{23}$-LL-F28249$\alpha$

In 3 mL of MeOH containing 0.04 g of $\Delta^{23}$-5-oxo-LL-F28249$\alpha$, 3.6 mg of NaBH$_4$ is added at room temperature. After 5 minutes, the mixture is evaporated to dryness and chromatographed on a silica gel preparative plate using CH$_2$Cl$_2$/EtOAc (20:1) to afford 0.0258 g of the title compound that is identified by mass spectrometry and NMR spectroscopy.

EXAMPLE 3

5-Oxo-LL-F28249$\alpha$

In 15 mL of anhydrous Et$_2$O, 3.5 g of activated MnO$_2$ is stirred under N$_2$ atmosphere, and 0.5 g of LL-F28249$\alpha$ is added in one portion. After stirring for 4 hours at room temperature (about 25° C.), the mixture is filtered through diatomaceous earth, and the filter cake is washed with Et$_2$O. The filtrate is evaporated to dryness to afford the title compound (0.23 g) that is characterized by mass spectrometry and NMR spectroscopy.

EXAMPLES 4 AND 5 $\Delta^{23}$-LL-F28249$\gamma$

The title compound is prepared by reacting LL-F28249$\gamma$ with diethylaminosulfur trifluoride by the method of Example 1 and identified by mass spectrometry and NMR spectroscopy.

Similarly, $\Delta^{23}$-LL-F28249$\gamma$ is prepared.

EXAMPLES 6–10

Using the procedures described in Example 3, the following 23-oxo-compounds are prepared:

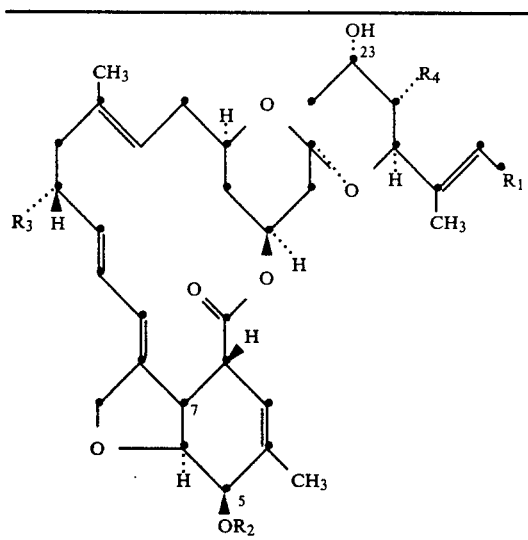

| R$_1$ | R$_3$ | R$_4$ |
|---|---|---|
| CH$_3$ | CH$_3$ | CH$_3$ |
| CH(CH$_3$)$_2$ | H | CH$_3$ |
| CH$_2$CH$_3$ | CH$_3$ | CH$_3$ |
| CH(CH$_3$)$_2$ | CH$_3$ | CH$_2$CH$_3$ |
| CH(CH$_3$)$_2$ | CH$_2$CH$_3$ | CH$_3$ |

EXAMPLES 11–15

Using the procedures described in Examples 1 and 2, the following 23-oxo-compounds are prepared:

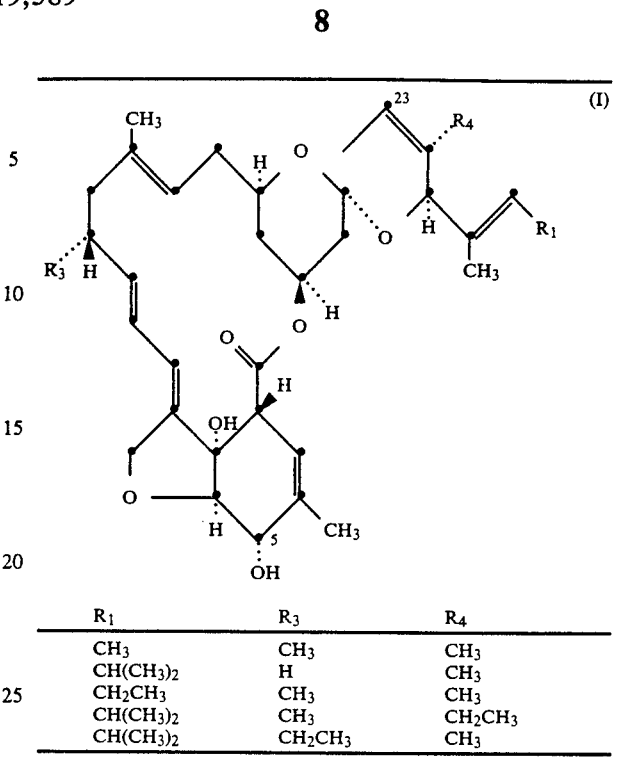

| R$_1$ | R$_3$ | R$_4$ |
|---|---|---|
| CH$_3$ | CH$_3$ | CH$_3$ |
| CH(CH$_3$)$_2$ | H | CH$_3$ |
| CH$_2$CH$_3$ | CH$_3$ | CH$_3$ |
| CH(CH$_3$)$_2$ | CH$_3$ | CH$_2$CH$_3$ |
| CH(CH$_3$)$_2$ | CH$_2$CH$_3$ | CH$_3$ |

What is claimed is:

1. A compound represented by structural formula (I):

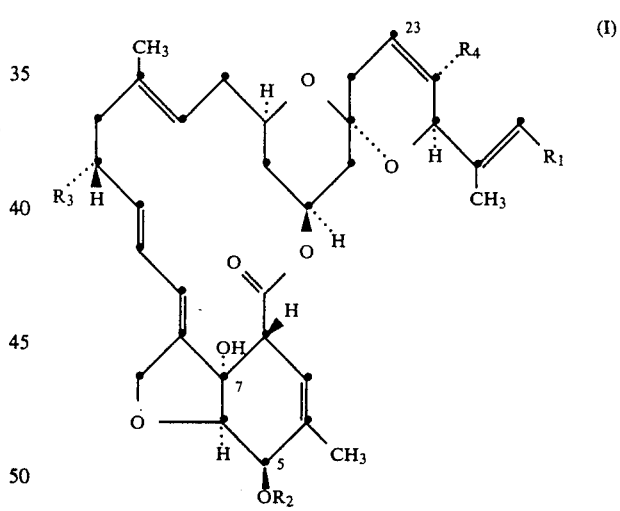

wherein R$_1$ is methyl, ethyl or isopropyl; R$_2$ is hydrogen or methyl; R$_3$ is hydrogen, methyl or ethyl; R$_4$ is methyl or ethyl; or a pharmaceutically and pharmacologically acceptable salt thereof; with the proviso that when R$_4$ is methyl, R$_3$ cannot be methyl.

2. A compound according to claim 1, wherein R$_1$ is isopropyl; R$_2$ is hydrogen or methyl; R$_3$ is methyl; and R$_4$ is ethyl.

3. A compound according to claim 2, wherein R$_1$ is isopropyl; R$_2$ is hydrogen; R$_3$ is methyl; and R$_4$ is ethyl.

4. A method for the prevention, treatment or control of parasitic infections in warm-blooded animals, said method comprising: orally, topically or parenterally administering to an animal infected with parasites, a parasitically-effective amount of a compound represented by structural formula (I),

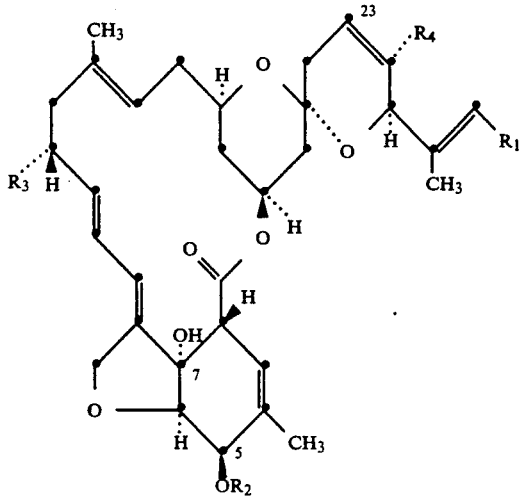
(I)

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof; with the proviso that when $R_4$ is methyl, $R_3$ cannot be methyl.

5. A method according to claim 4, wherein said compound has $R_1$ as isopropyl; $R_2$ is hydrogen or methyl; $R_3$ is methyl; and $R_4$ is ethyl.

6. A method according to claim 5, wherein said compound has $R_1$ as isopropyl; $R_2$ is hydrogen; $R_3$ is methyl; and $R_4$ is ethyl.

7. A method for protecting crops, trees, shrubs, stored grain and ornamentals from attack by acarids or insects which infest them, said method comprising: applying an acaricidally or insecticidally-effective amount of a compound represented by structural formula (I),

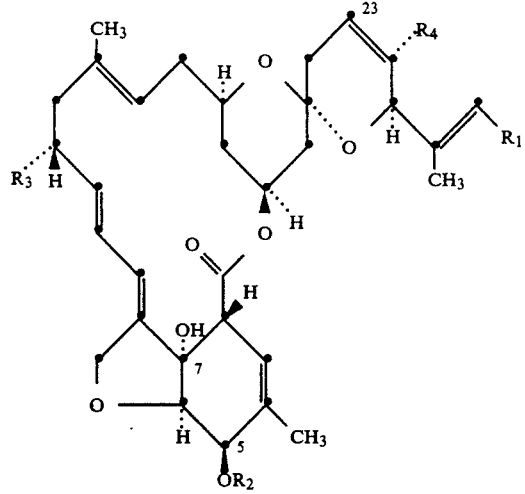
(I)

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof; with the proviso that when $R_4$ is methyl, $R_3$ cannot be methyl.

8. A method according to claim 7, wherein said compound is applied to the foliage of crops and plants, the soil in which they are grown or the trunk thereof.

9. A method according to claim 8, wherein said compound has $R_1$ as isopropyl; $R_2$ is hydrogen or methyl; $R_3$ is methyl; and $R_4$ is ethyl.

10. A method according to claim 9, wherein said compound is $R_1$ as isopropyl; $R_2$ is hydrogen; $R_3$ is methyl; and $R_4$ is ethyl.

11. A method for the control of plant nematodes, said method comprising: applying to the foliage of plants, the soil in which they are grown or into the trunks thereof, a nematocidally-effective amount of a compound represented by structural formula (I),

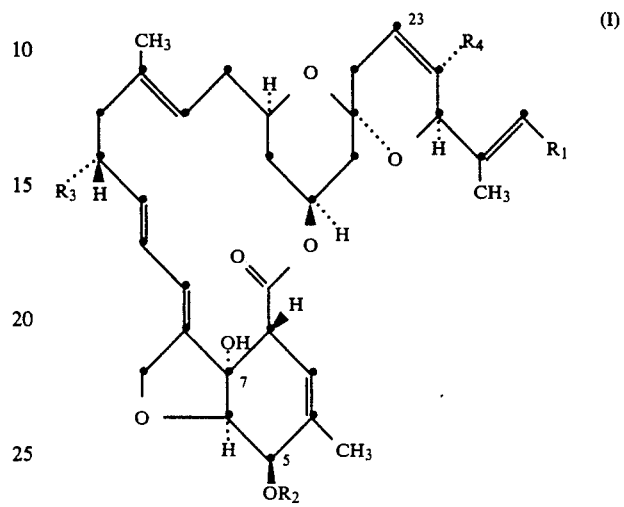
(I)

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof; with the proviso that when $R_4$ is methyl, $R_3$ cannot be methyl.

12. A method according to claim 11, wherein said compound has $R_1$ as isopropyl; $R_2$ is hydrogen or methyl; $R_3$ is methyl; and $R_4$ is ethyl.

13. A method according to claim 12, wherein said compound has $R_1$ as isopropyl; $R_2$ is hydrogen; $R_3$ is methyl; and $R_4$ is ethyl.

14. A composition for the treatment, prevention or control of parasitic infections in warm-blooded animals or for the control of insects, said composition comprising: a pharmacologically or insecticidally-effective amount of a compound represented by structural formula (I),

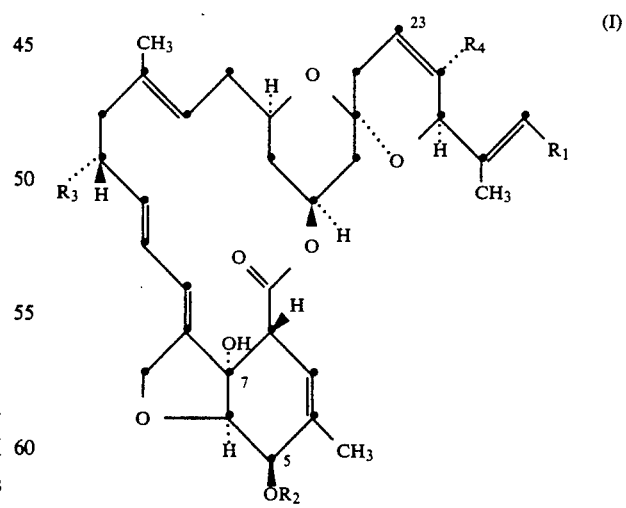
(I)

wherein $R_1$ is methyl, ethyl or isopropyl; $R_2$ is hydrogen or methyl; $R_3$ is hydrogen, methyl or ethyl; $R_4$ is methyl or ethyl; or a pharmaceutically and pharmacologically acceptable salt thereof; and an inert carrier; with the proviso that when $R_4$ is methyl, $R_3$ cannot be methyl.

* * * * *